US008906624B2

(12) United States Patent
Seo et al.

(10) Patent No.: US 8,906,624 B2
(45) Date of Patent: Dec. 9, 2014

(54) ROTATIONAL PCR EQUIPMENT AND PCR METHOD USING THE SAME

(75) Inventors: Tae Seok Seo, Daejeon (KR); Jae Hwan Jung, Daejeon (KR); Seok Jin Choi, Daejeon (KR)

(73) Assignee: Korea Advanced Institute of Science and Technology (KAIST), Daejeon (KR)

( * ) Notice: Subject to any disclaimer, the term of this patent is extended or adjusted under 35 U.S.C. 154(b) by 113 days.

(21) Appl. No.: 12/965,585

(22) Filed: Dec. 10, 2010

(65) Prior Publication Data

US 2011/0244522 A1 Oct. 6, 2011

(30) Foreign Application Priority Data

Mar. 30, 2010 (KR) ........................ 10-2010-0028294
Aug. 17, 2010 (KR) ........................ 10-2010-0079474

(51) Int. Cl.

*C12Q 1/68* (2006.01)
*C12P 19/34* (2006.01)
*G01N 15/06* (2006.01)
*G01N 9/30* (2006.01)
*B01L 7/00* (2006.01)
*B01L 3/00* (2006.01)

(52) U.S. Cl.

CPC ......... *B01L 7/5255* (2013.01); *B01L 3/502761* (2013.01); *B01L 2300/0867* (2013.01); *B01L 2300/161* (2013.01); *B01L 2300/0819* (2013.01); *B01L 2300/0864* (2013.01); *B01L 2400/088* (2013.01); *B01L 2400/0677* (2013.01); *B01L 2400/0409* (2013.01); *B01L 2300/0803* (2013.01)

USPC ............ 435/6.12; 435/6.1; 435/6.11; 422/50; 422/68.1; 422/72

(58) Field of Classification Search

None

See application file for complete search history.

(56) References Cited

U.S. PATENT DOCUMENTS

2005/0026277 A1* 2/2005 Festoc ........................ 435/287.2
2009/0035847 A1* 2/2009 Cho et al. ................... 435/289.1

FOREIGN PATENT DOCUMENTS

WO WO 0242430 A1 * 5/2002

* cited by examiner

*Primary Examiner* — Young J Kim

(74) *Attorney, Agent, or Firm* — Rabin & Berdo, P.C.

(57) ABSTRACT

Provided are a rotational PCR apparatus, a PCR chip for the same and a rotational PCR method using the same.

The disclosed rotational PCR apparatus includes: a PCR chip where PCR is performed; a rotating means connected to the PCR chip and rotating the PCR chip; and a temperature zone forming means spaced apart from the PCR chip, capable of applying thermal energy to the PCR chip and allowing the rotating PCR chip to pass through different temperature zones. The rotational PCR apparatus and method allow performance of PCR with wanted temperature condition and cycles by rotating the chip containing the target substance. Accordingly, a high-efficiency PCR process may be accomplished at low cost. Further, since the target substance can be effectively separated and purified utilizing the centrifugal force resulting from the rotating platform, separation and purification may be achieved economically without requiring additional equipments.

8 Claims, 11 Drawing Sheets

ROTATIONAL PCR EQUIPMENT AND PCR METHOD USING THE SAME

CROSS-REFERENCE TO RELATED APPLICATIONS

This application claims priority under 35 U.S.C. §119 to Korean Patent Application No. 10-2010-0079474 filed on Aug. 17, 2010 and Korean Patent Application No. 10-2010-0028294 filed on Mar. 30, 2010 in the Korean Intellectual Property Office, the disclosure of which is incorporated herein by reference in its entirety.

TECHNICAL FIELD

The present disclosure relates to a rotational PCR apparatus, a PCR chip for the same and a rotational PCR method using the same. More particularly, the disclosure relates to a rotational PCR apparatus capable of performing PCR processes under desired temperature conditions by rotating a PCR chip and capable of effectively performing separation and purification of sample by rotating the chip, the PCR chip for the same and a rotational PCR method using the same.

BACKGROUND

DNA amplification techniques are widely utilized in the fields of bioscience, genetic engineering and medicine for the purposes of research, development and diagnosis. Especially, the DNA amplification technique based on polymerase chain reaction (PCR) is widely employed. PCR is used to amplify a particular DNA sequence as desired. The first step of PCR is to denature DNA. A double-stranded DNA is split by heating. Each separated DNA strand serves as a template. The second step of PCR is annealing. In this step, primers are annealed to the template DNA. The annealing temperature is an important factor determining the accuracy of the reaction. If the temperature is too high, the quantity of amplified DNA products decreases drastically because the primers are too weakly bound to the template DNA. And, if the temperature is too low, unwanted DNA may be amplified due to nonspecific binding of the primers. The third PCR step of PCR is elongation. At this step, a thermostable DNA polymerase synthesizes new DNA from the template DNA. The PCR may be classified into DNA PCR and RNA PCR. Usually, the purpose of amplifying genes by PCR is to observe particular sequences in the genes, not the entire genes. In such PCR techniques, it is very important to form accurate temperature gradients for the respective PCR steps and to maintain them.

SUMMARY

The present disclosure is directed to providing a rotational PCR apparatus which performs PCR by rotating a chip including a target sample to be analyzed and the PCR chip for the same.

The present disclosure is also directed to providing a rotational PCR method allowing to perform pretreatment of the target sample and PCR on the same platform.

In one general aspect, the present disclosure provides a PCR apparatus including: a PCR chip where PCR is performed; a rotating means connected to the PCR chip and rotating the PCR chip; and a temperature zone forming means spaced apart from the PCR chip, capable of applying thermal energy to the PCR chip and allowing the rotating PCR chip to pass through different temperature zones.

In another general aspect, the present disclosure provides a PCR method using a PCR chip, comprising: performing PCR by allowing a PCR chip containing a target substance to pass through a plurality of temperature zones at different temperatures.

The present disclosure also provides a PCR method using a PCR chip having a pretreatment unit and a PCR unit, which includes: performing pretreatment of separating the target substance from a sample solution by sequentially flowing the sample solution, a washing buffer and an elution buffer from the pretreatment unit of the PCR chip to silica beads; introducing the separated target substance into the PCR unit connected at the rear end of the pretreatment unit; and performing PCR by rotating the target substance introduced into the PCR unit through a plurality of temperature zones.

Other features and aspects will be apparent from the following detailed description, the drawings, and the claims.

BRIEF DESCRIPTION OF THE DRAWINGS

The above and other objects, features and advantages of the present disclosure will become apparent from the following description of certain exemplary embodiments given in conjunction with the accompanying drawings, in which.

Figure 1:
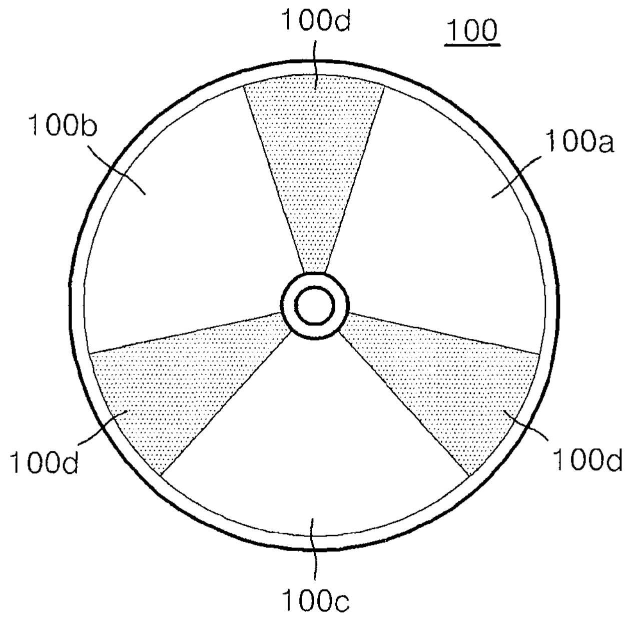
FIG. 1 is a front view of a temperature zone forming means 100 according to an embodiment of the present disclosure.

It should be understood that the appended drawings are not necessarily to scale, presenting a somewhat simplified representation of various preferred features illustrative of the basic principles of the disclosure. The specific design features of the disclosure as disclosed herein, including, for example, specific dimensions, orientations, locations and shapes, will be determined in part by the particular intended application and use environment.

In the figures, reference numerals refer to the same or equivalent parts of the disclosure throughout the several figures of the drawings.

DETAILED DESCRIPTION OF EMBODIMENTS

The advantages, features and aspects of the present disclosure will become apparent from the following description of the embodiments with reference to the accompanying drawings, which is set forth hereinafter. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. The terminology used herein is for the purpose of describing particular embodiments only and is not intended to be limiting of the example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

The present disclosure provides a PCR apparatus and a PCR method allowing a chip (hereinafter, "PCR chip") containing a target substance (i.e., DNA or RNA) of PCR to pass through a plurality of temperature zones at different temperatures. For this, the PCR chip is rotated to pass thorough the temperature zones arranged in circular shape.

As used herein, the term "temperature gradient zone" or "temperature zone" refers to a spatial region where a specific temperature is maintained. In an embodiment of the present disclosure, the temperature zones may be formed by a heating metal block, as a temperature zone forming means, spaced apart above and/or below from the PCR chip and capable of applying thermal energy to the PCR chip. In another embodiment of the present disclosure, alight source capable of generating light energy such as infrared rays may be used as the temperature zone forming means. However, the present disclosure is not limited to those examples, and any means capable of applying a certain level of thermal energy to the rotating PCR chip may be used as the temperature zone forming means, which is included within the scope of the present disclosure.

Hereinafter, exemplary embodiments of the present disclosure will be described in detail with reference to the accompanying drawings.

Figure 2:
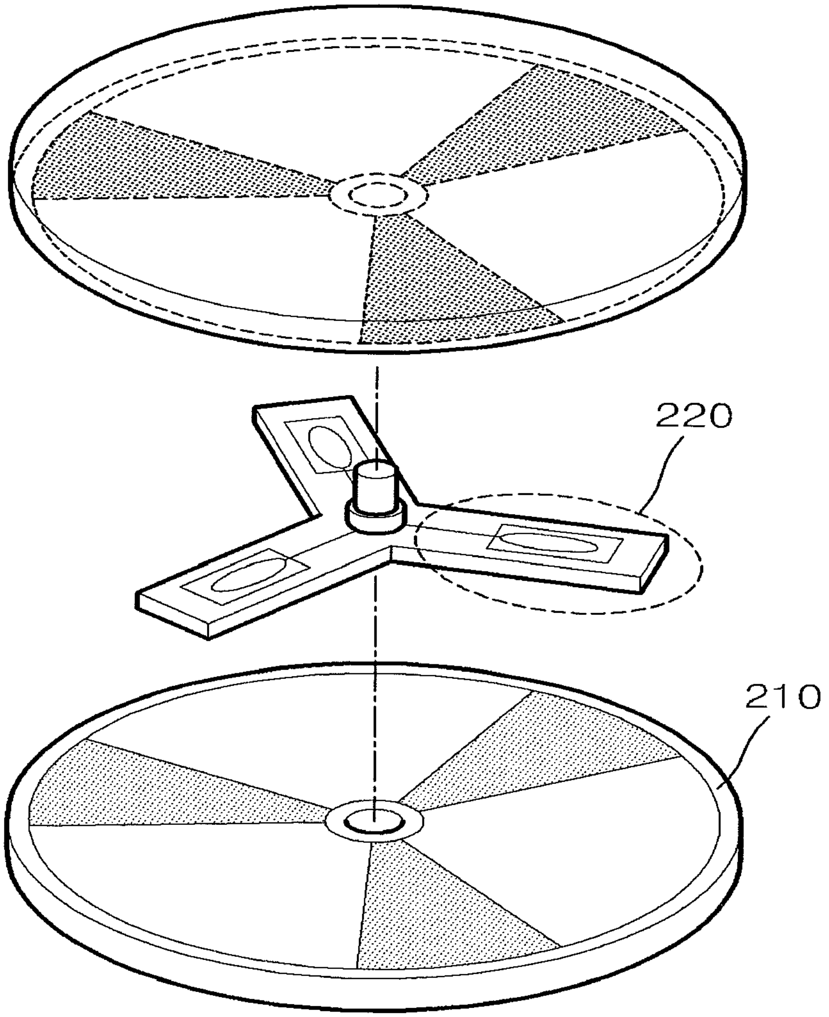
FIGS. 2 to 4 are perspective views of a PCR apparatus comprising the temperature zone forming means 100 of FIG. 1 and a PCR chip 220.

FIG. 1 is a front view of a temperature zone forming means 100 according to an embodiment of the present disclosure. FIG. 2 is a perspective view of a PCR apparatus comprising the temperature zone forming means 100 of FIG. 1 and a PCR chip 220, FIG. 3 is a perspective view of a chip module comprising three PCR chips, and FIG. 4 is a perspective view of a PCR chip module coupled with a rotating means.

Referring to FIG. 1, the temperature zone forming means of the PCR apparatus according to this embodiment may be in the form of a wheel or disc comprising a plurality of heating metal blocks (hereinafter, "heating blocks") the temperature of which is independently controllable. Between the heating blocks 100*a*, 100*b*, 100*c*, an insulator 100*d* and/or a cooling block for preventing thermal conduction between the heating blocks may be provided. In an embodiment of the present disclosure, heat may be applied to the heating blocks by means of an electric heater using a resistor, but the scope of the present disclosure is not limited thereto.

The temperature zone forming means 100 comprises a plurality of independent heating means (i.e., the heating blocks). By varying the temperature condition of the heating blocks, a rotating PCR chip spaced apart from the heating blocks may be heated at different temperatures.

Figure 3:
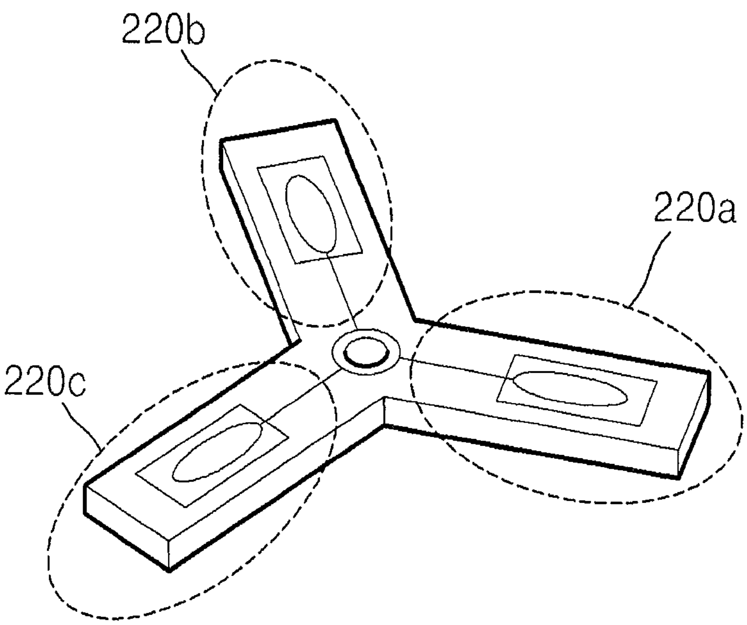
Figure 4:
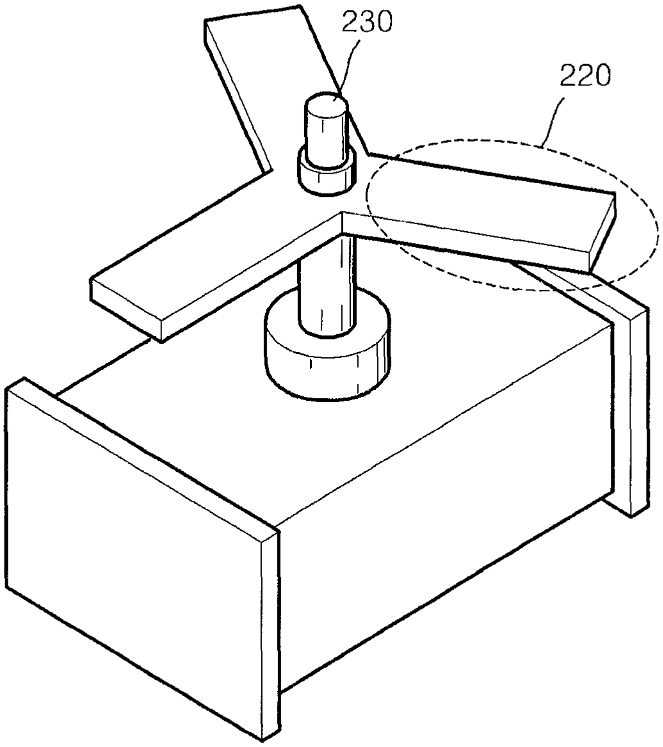

Referring to FIGS. 2 and 4, the PCR apparatus comprises the rotating means to rotate the PCR chip of FIG. 3. In an embodiment of the present disclosure, the apparatus may comprise a motor (not shown) and a shaft 230, which is connected to the motor and rotates, as the rotating means.

In an embodiment of the present disclosure, one or more rotating PCR chip(s) 220 rotating as the shaft rotates may be coupled with the shaft 230. In FIG. 3, a chip module comprising three PCR chips 220*a*, 220*b*, 220*c* is illustrated.

In the PCR chip 220, a PCR cocktail solution containing a target sample (e.g., DNA or RNA) to be amplified, a primer, etc. flows. For this, the PCR chip 220 may be equipped with an inlet and an outlet through which the sample solution is introduced and discharged. A chamber unit wherein PCR occurs may be provided between the inlet and the outlet.

A heating block 210 in the form of a disc, which is the temperature zone forming means, is provided spaced apart from the PCR chip 220. One or more of the temperature zone forming means 210 may be provided for one PCR apparatus. In an embodiment, two temperature zone forming means 210 may face each other with the chip therebetween. However, the scope of the present disclosure is not limited thereto.

In an embodiment of the present disclosure, the heating block may comprise at least one heating block group(s) comprising three unit heating blocks so as to form at least three temperature zones. It is because one cycle of a PCR procedure passes through three temperature steps, in general. In an embodiment of the present disclosure, three temperature zones are formed by the plurality of heating blocks, at temperatures 95° C., 72° C. and 55° C., respectively. As the rotating PCR chip passes through the temperature zones, PCR occurs under the corresponding temperature conditions. Although the number of the temperature gradient zones formed by the heating block shown in the embodiment with reference to FIGS. 2 to 4 is three, it may be increased further. In this case, a plurality of PCR cycles may occur while the PCR chip rotates 360°. Thus, a plurality of PCR cycles may be performed at once simply by rotating a plurality of PCR chips once.

Figure 5:
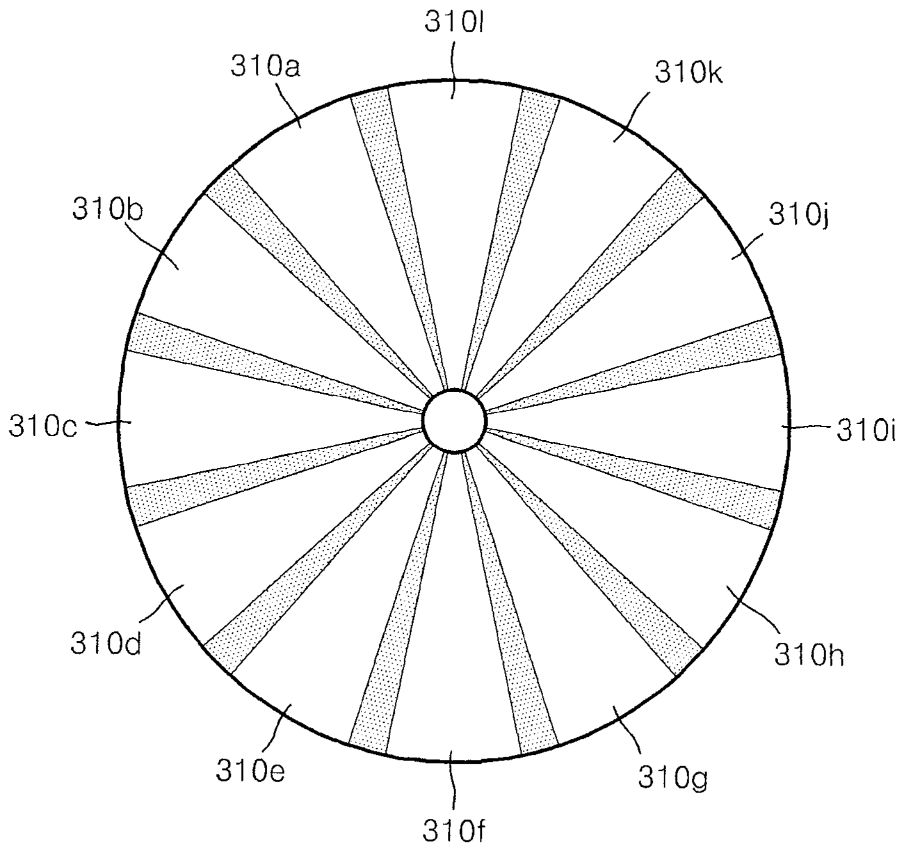
FIG. 5 is a front view of a PCR apparatus according to another embodiment of the present disclosure.

FIG. 5 is a front view of a PCR apparatus according to another embodiment of the present disclosure.

Referring to FIG. 5, a temperature zone forming means 310 of a PCR apparatus according to this embodiment comprises a plurality of heating block groups comprising three unit heating blocks. A first heating block group 310*a*, 310*b*, 310*c* is controlled under a temperature condition corresponding to one PCR cycle and a second heating block group 310*d*, 310*e*, 310*f* is also controlled under the same temperature condition corresponding to one PCR cycle. The remaining heating block groups 310*g* to 310*l* are also controlled under the same temperature condition.

As a PCR chip rotates from 310*a* to 310*l*, the sample in the PCR chip passes through four PCR cycles. If a plurality of PCR chips are rotated from 310*a*, 310*d*, 310*g* and 310*j* (These correspond to the temperature zones where PCR is initiated.), four samples pass through four PCR cycles with just one rotation. As such, the present disclosure provides a highly efficient chip-based PCR apparatus.

The PCR apparatus according to the present disclosure also provides a new concept of performing separation and purification of the sample (sample pretreatment), which is required for PCR analysis, on the same platform using the centrifugal force occurring as the PCR chip rotates.

In general, a pretreatment process of separating and purifying the target substance, e.g. DNA or RNA, is required for a PCR procedure. Usually, a solid-phase capture approach using a capturing means capable of selectively capturing the target sample only, for example, silica beads, is employed. This pretreatment method comprises: a first step of flowing a sample containing the target substance to be captured to a capturing means (e.g., silica beads) so as to adsorb the target substance onto the silica beads; a second step of removing components other than the target substance to be amplified from the capturing means by washing; and a third step of separating the target substance captured by the capturing means. In general, the second step is performed by flowing a washing buffer to the silica beads, and the third step is performed by flowing an elution buffer to the silica beads.

In a PCR process according to an embodiment of the present disclosure, the pretreatment for separating the target substance such as RNA and DNA is performed by flowing a mixture solution (sample solution) containing the target substance to a capturing means such as silica beads. In particular, noting that the mixture solution as well as the washing buffer and the elution buffer is flown toward one direction, i.e. toward the capturing means (silica beads), the cross-sectional areas of channels of the solutions from the respective solution chambers holding and storing the solutions are set differently, so that only the wanted solution may flow toward the capturing means by varying the rotation speed. For this, in an embodiment of the present disclosure, the solution channels are hydrophobically treated, so that the aqueous solutions may flow through the hydrophobic channels only when a force exceeding a predetermined value is applied thereto. However, the scope of the present disclosure is not limited thereto, and any possible means allowing selective control of the flow of the solutions based on the difference in centrifugal force are included within the scope of the present disclosure.

Figure 6:
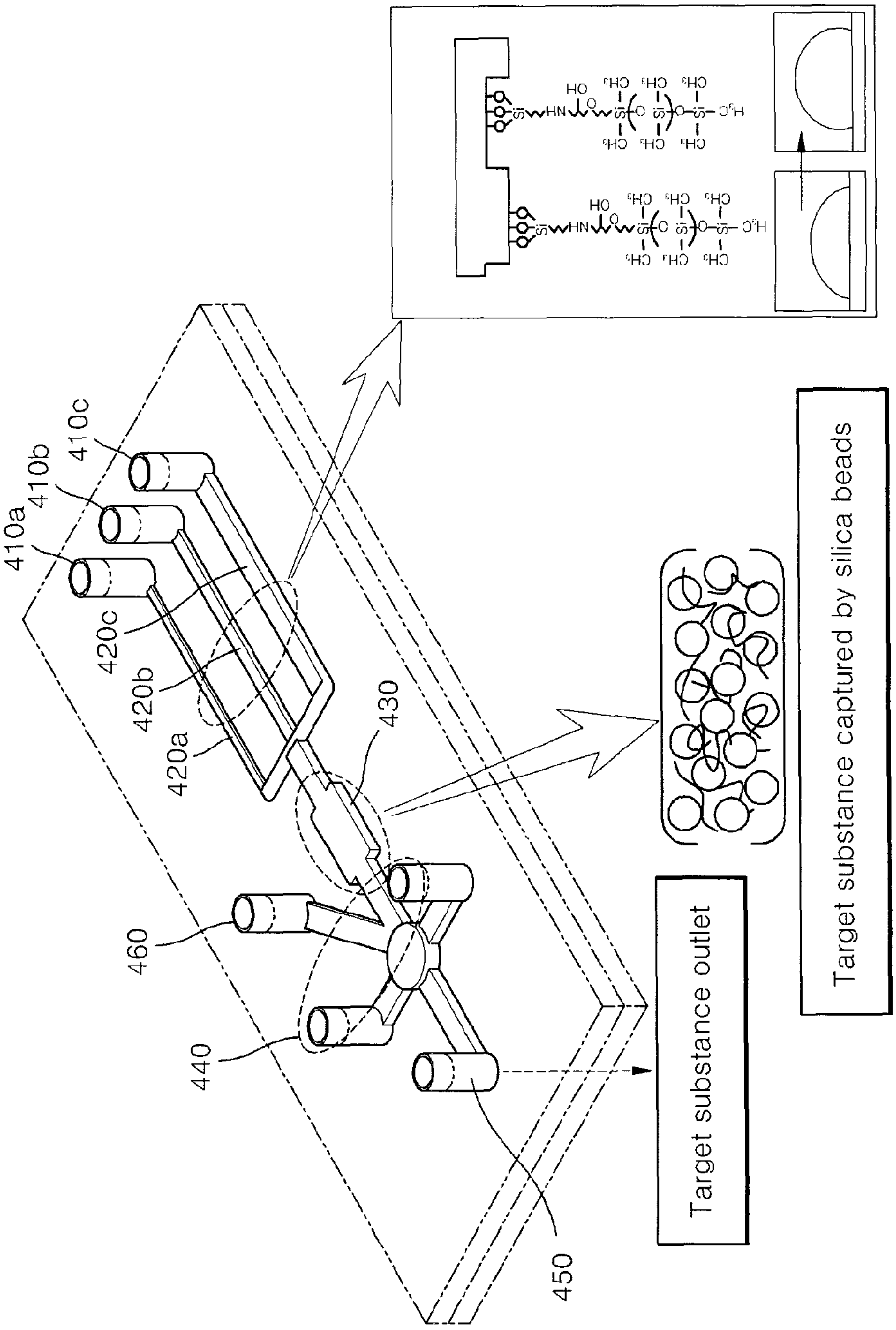
FIG. 6 is a partial schematic view of a pretreatment unit of a PCR chip according to an embodiment of the present disclosure.

The PCR chip according to the present disclosure may further comprise, in addition to the PCR unit where PCR occurs, and a pretreatment unit connected to the fore end of the PCR unit, where the target substance is separated from the sample solution. FIG. 6 is a partial schematic view of a pretreatment unit of a PCR chip according to an embodiment of the present disclosure.

Referring to FIG. 6, a pretreatment unit of a PCR chip according to an embodiment of the present disclosure has three solution chambers 410*a*, 410*b*, 410*c* each containing different solution. Fluid channels 420*a*, 420*b*, 420*c* connected to the chambers are hydrophobically treated. As such, the three aqueous solutions (sample solution, washing buffer and elution buffer) cannot normally flow through the hydrophobically treated channels, unless a force exceeding a predetermined value is applied thereto. The enlarged portion of the hydrophobic channels 420*a*, 420*b*, 420*c* in FIG. 6 shows that the channels from the solution chambers are hydrophobically treated with a siloxane-based compound. However, the scope of the present disclosure is not limited thereto.

It is to be noted that the force needed to move the solutions changes depending on the size (cross-sectional area) of the hydrophobically treated fluid channels. The force needed to move the liquids is obtained from the centrifugal force resulting from the rotation of the PCR chip comprising the pretreatment unit, which will be described in detail hereinbelow.

The hydrophobic channels 420*a*, 420*b*, 420*c* are commonly connected to silica beads 430 to which the target substance is selectively bound. The solutions flowing through the hydrophobic channels 420*a*, 420*b*, 420*c* are introduced to the silica beads 430. Thereafter, the target substance captured by the silica beads 430 moves, as a valve 440 that can be selectively opened/closed by heat is opened, through an outlet 450 to the PCR unit at the rear end due to the centrifugal force resulting from the rotation of the PCR chip. Then, PCR proceeds as described referring to FIGS. 1 to 5.

A discharge port 460 may be further provided to discharge the solution remaining after washing the silica beads to outside. That is, while the valve 440 is closed, the solution (e.g., washing buffer) discharged from the silica beads 430 is discharged to outside through the discharge port 460.

Figure 7:
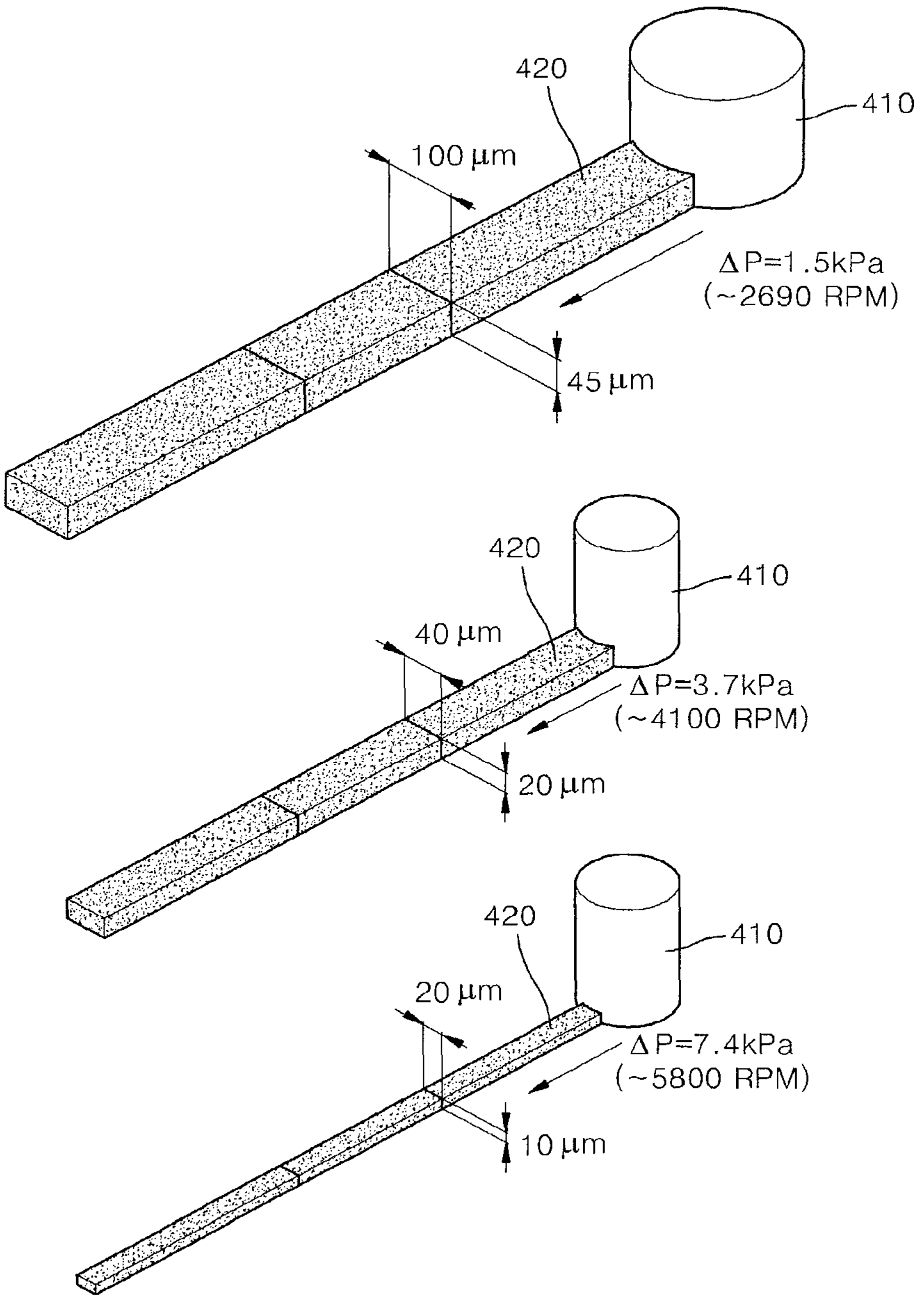
FIG. 7 shows configurations of solution chambers and hydrophobic channels according to an embodiment of the present disclosure.

FIG. 7 shows configurations of solution chambers and hydrophobic channels according to an embodiment of the present disclosure.

Referring to FIG. 7, if the hydrophobic channel 420 has a large cross-sectional area, the fluid in the solution chamber (the upper chamber in FIG. 7) may be flown with a relatively smaller force (1.5 kPa). However, if the cross-sectional area is smaller, a larger force is required for the fluid to flow. In the present disclosure, the force needed to move the solution is attained from the centrifugal force resulting from the rotation of the PCR chip including the pretreatment unit.

First, when the PCR chip including the pretreatment unit rotates relatively slowly, a relatively smaller force is applied to the solution chamber 410. Thus, the solution in the solution chamber (the upper chamber in FIG. 7) connected to the hydrophobic channel with the largest cross-sectional area flows first. For example, whereas the solution in the lower solution chamber 410*c* of FIG. 6 may flow through the hydrophobic channel with a rotation speed of 2690 rpm, the intermediate solution chamber 410*b* and the upper solution chamber 410*a* may respectively require rotation speeds of 4100 rpm and 5800 rpm.

Accordingly, in an embodiment of the present disclosure, the hydrophobic channel for the sample solution which needs to be flown to the silica beads first has the largest cross-sectional area. As such, when the rotation speed of the PCR chip becomes equal to or greater than a first speed, the sample solution flows from the sample solution chamber to the silica beads. The hydrophobic channel for the washing buffer which needs to be flown secondly has the second largest cross-sectional area. As such, when the rotation speed of the PCR chip exceeds the first speed and becomes equal to or greater than a second speed, the washing buffer flows through the hydrophobic channel to the silica beads. As a result, all the components other than the target substance adsorbed to the silica beads are removed and discharged to outside through the discharge port 460. Then, the elution buffer for separating the target substance adsorbed to the silica beads is flown to the silica beads. The hydrophobic channel for the elution buffer has a cross-sectional area smaller than those of the channels for the sample solution and the washing buffer. Thus, when the rotation speed of the PCR chip exceeds the second speed and becomes equal to or greater than a third speed, the elution buffer flows through the hydrophobic channel connected to the corresponding chamber to the silica beads. As a result, the target substance such as DNA or RNA adsorbed to the silica beads is separated from the silica beads.

Noting that both the PCR process and the pretreatment process are carried out as the PCR chip rotates, the present disclosure provides a new-concept integrated PCR chip wherein a PCR unit and a pretreatment unit are integrated in a single chip.

Figure 8:
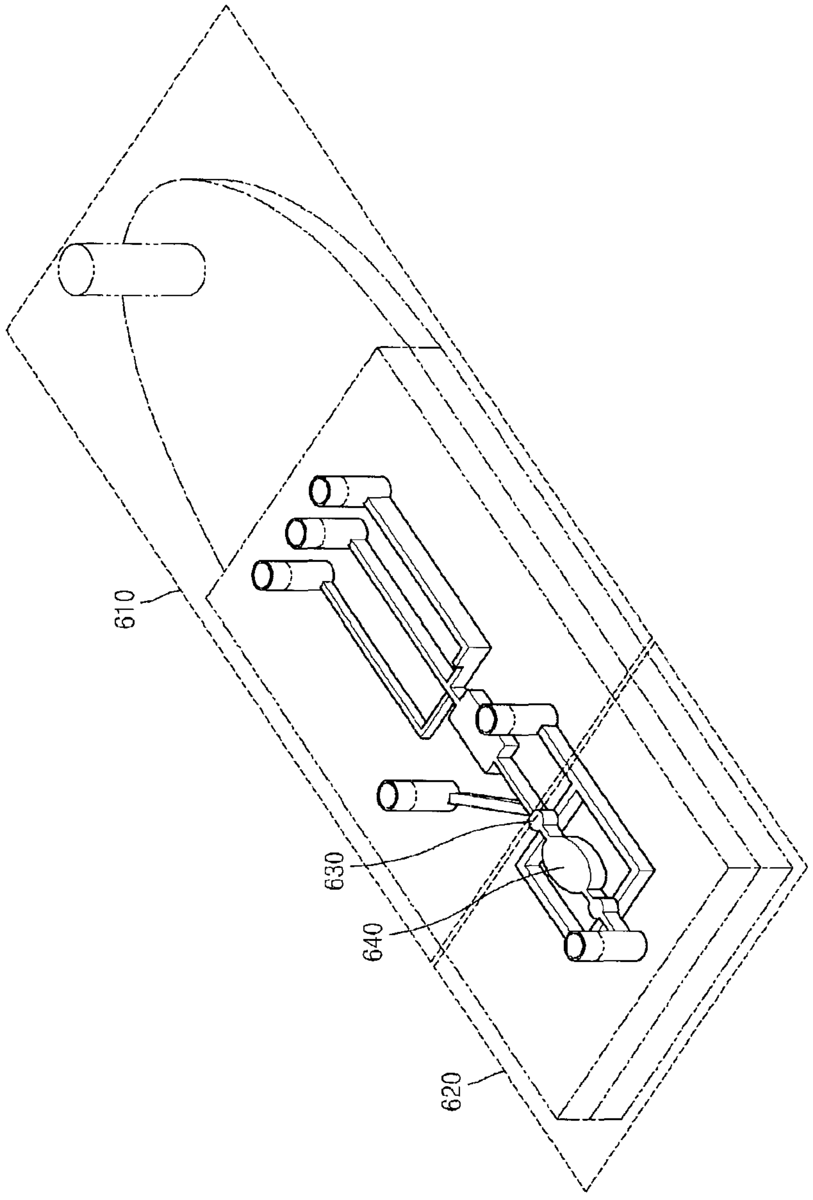
FIG. 8 is a perspective view of an integrated PCR chip according to an embodiment of the present disclosure.

FIG. 8 is a perspective view of an integrated PCR chip according to an embodiment of the present disclosure.

Referring to FIG. 8, a pretreatment unit 610 described in FIG. 6 and a PCR unit 620 corresponding to the PCR chip 220 in FIG. 2 are coupled with each other. Between the pretreatment unit 610 and the PCR unit 620, a thermoreactive polymer valve 630 is provided. As the thermoreactive polymer valve 630 is opened, the separated and purified target substance is introduced from an outlet of the pretreatment unit 610 to the PCR unit 620. Then, PCR is carried out in a PCR chamber 640. As the PCR chip rotates, a plurality of PCR cycles occur, as described earlier.

As described, the PCR chip according to this embodiment has the pretreatment unit for separating and purifying DNA or RNA and the PCR unit where PCR occurs. The target substance separated by the pretreatment unit flows through the thermoreactive polymer valve 630, which is opened at low temperature, and is introduced into the PCR unit. Thereafter, the target substance introduced to the PCR unit is heated by heating blocks and PCR occurs. In a PCR apparatus according to an embodiment of the present disclosure, the valve 630 connecting the pretreatment unit and the PCR unit is closed as temperature rises. In this case, backflow of the target substance to the pretreatment unit may be prevented during the PCR process occurring at high temperature.

A more detailed description will be given about the thermoreactive valve and the pretreatment unit.

In an embodiment of the present disclosure, the thermoreactive valve comprises a thermoreactive polymer. More specifically, Fluorinert FC40 available from 3M may be used. The thermoreactive polymer expands above a predetermined temperature, e.g. about 40° C., thereby pushing a flexible membrane contacting with the thermoreactive polymer toward a fluid channel. As a result, the fluid channel is blocked. Conversely, below a predetermined temperature, e.g. about 40° C., the thermoreactive polymer is shrunken and the pretreatment unit is communicated with the PCR unit again.

Figure 9:
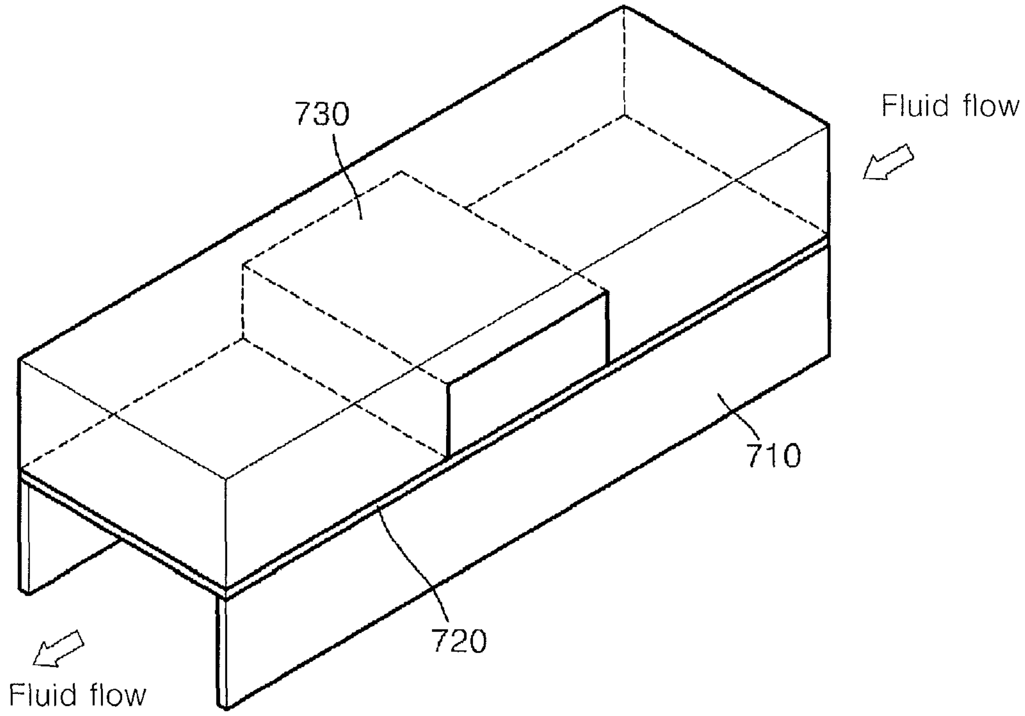
FIGS. 9 and 10 are cross-sectional views of a pretreatment unit of a PCR chip according to an embodiment of the present disclosure.
Figure 10:
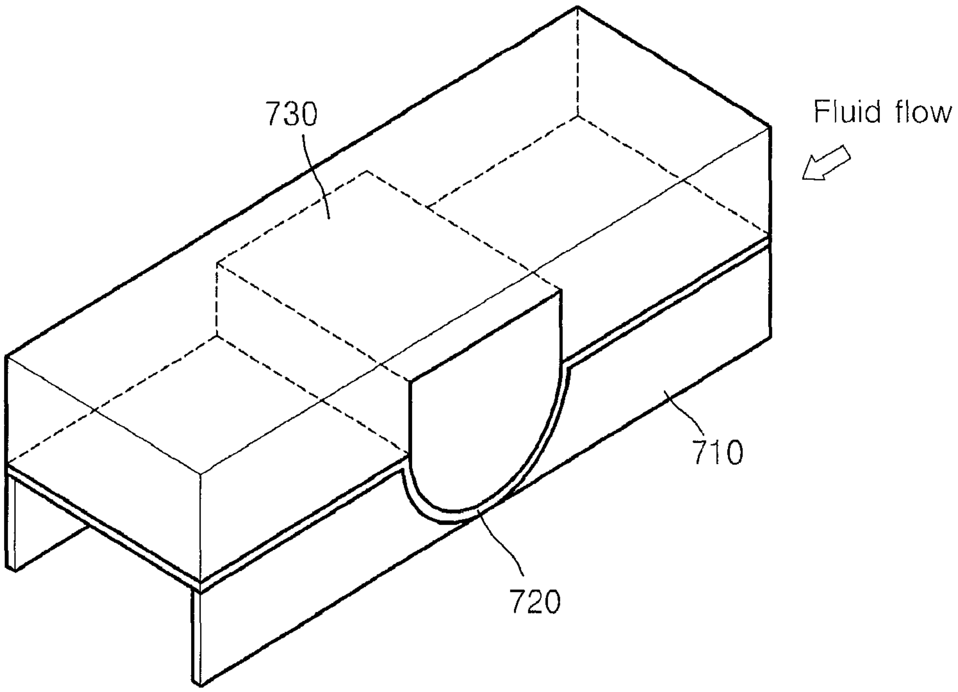

FIGS. 9 and 10 are cross-sectional views of a pretreatment unit of a PCR chip according to an embodiment of the present disclosure.

Referring to FIG. 9, the PCR chip comprises three layers—a sample layer 710 with a channel allowing the flow of a target substance formed, a polymer layer 730 comprising a thermoreactive polymer expanding/shrinking depending on the temperature condition, and a flexible membrane 720 provided between the sample layer 710 and the polymer layer 730 and comprising a flexible material that can move elastically according to the expansion/shrinkage of the polymer layer, such as polydimethylsiloxane (PDMS). As seen in FIG. 9, the thermoreactive polymer layer 730 does not expand at room temperature. Thus, a sample solution may through the channel of the sample layer 710 therebelow.

However, referring to FIG. 10, the thermoreactive polymer layer 730 expands as temperature rises. As the polymer layer 730 expands, the flexible membrane 720 therebelow also expands downward. As a result, the fluid channel of the sample layer 710 is blocked and closed by the flexible membrane 720 expanding downward. Since PCR occurs at temperatures above 40° C., thermoreactive valve remains closed during the PCR process. Accordingly, the PCR process occurs stably in the PCR unit without leakage of fluid to the pretreatment unit.

According to the PCR method of the present disclosure using the PCR chip, PCR occurs while the PCR chip containing the target substance rotates and passes through a plurality of temperature zones at different temperatures. For this, in an embodiment of the present disclosure, the plurality of temperature zones is arranged such that temperatures required for PCR are repeated. The temperatures of the temperature zones may be maintained by a heating means (e.g. heating blocks) spaced apart from the PCR chip, as described earlier.

Figure 11:
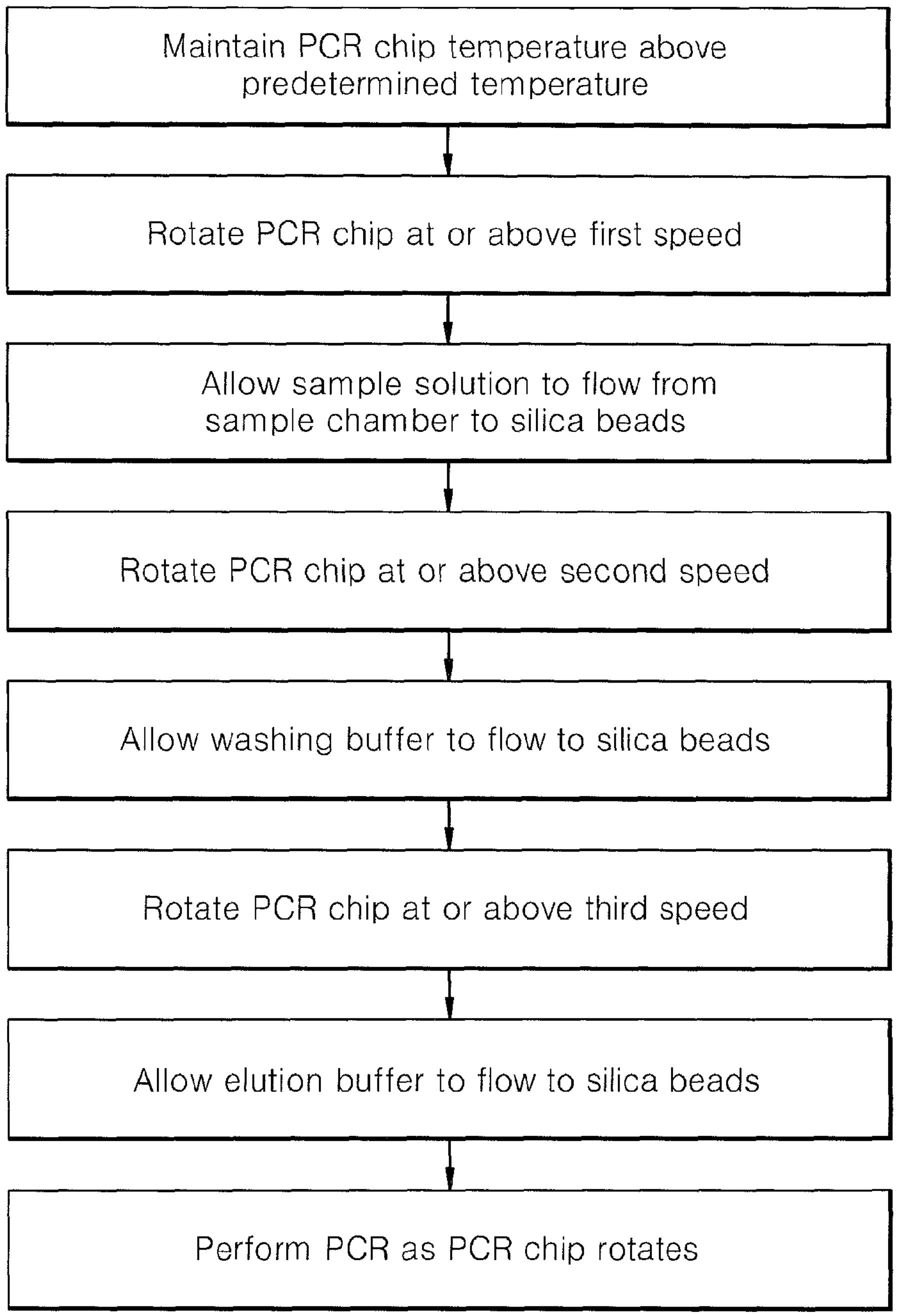
FIG. 11 is a flow diagram of a PCR method using a PCR chip according to another embodiment of the present disclosure.

FIG. 11 is a flow diagram of a PCR method using a PCR chip according to another embodiment of the present disclosure.

Referring to FIG. 11, first, a PCR chip comprising a pretreatment unit where a target substance is separated and a PCR unit where PCR occurs for the separated target substance is rotated at or above a first speed, with the chip temperature maintained above a certain temperature. Under this temperature condition, a thermoreactive valve connecting the pretreatment unit and the PCR unit is closed, and no solution flows from the pretreatment unit to the PCR unit.

As the chip rotates at or above the first speed, only a sample solution (an aqueous mixture solution containing the target substance) flows from a sample solution chamber having a hydrophobic channel with the largest cross-sectional area to silica beads, which are a capturing means. Then, the chip is rotated at or above a second speed. As the chip rotates at or above the second speed, a washing buffer (a solution for removing components other than the target substance from the silica beads) flows to the silica beads. The components other than the target substance are removed from the silica beads by the washing buffer. Then, the chip is rotated at or above a third speed. As the chip rotates at or above the third speed, an elution buffer flows through a hydrophobic channel with the smallest cross-sectional area to silica beads. As a result, the target substance is separated from the silica beads. The separated target substance is introduced to the PCR unit. In order to introduce the target substance into the PCR unit, the temperature of the PCR chip needs to be lowered to open the thermoreactive valve between the PCR unit and the pretreatment unit. The valve may be opened before, after or during the flow of the elution buffer, as long as the target substance separated from the silica beads by the elution buffer may be introduced into the PCR unit.

Then, PCR occurs as the PCR chip rotates. As described with reference to FIGS. 1 to 5, the PCR process occurs while the PCR chip passes through a plurality of temperature gradient zones. At this time, in order to prevent backflow of the solution to the pretreatment unit, the thermoreactive valve is closed as the PCR chip is maintained above a predetermined temperature.

The present disclosure further provides a PCR system comprising the above-described integrated PCR chip and a rotating platform with a plurality of temperature zones formed thereon.

The rotational PCR apparatus and method according to the present disclosure allow performance of PCR with wanted temperature condition and cycles by rotating the chip containing the target substance. Accordingly, a high-efficiency PCR process may be accomplished at low cost. Further, since the target substance can be effectively separated and purified utilizing the centrifugal force resulting from the rotating platform, separation and purification may be achieved economically without requiring additional equipments.

While the present disclosure has been described with respect to the specific embodiments, it will be apparent to those skilled in the art that various changes and modifications may be made without departing from the spirit and scope of the disclosure as defined in the following claims.

What is claimed is:

1. A PCR apparatus comprising:

a PCR module which comprises at least one radially distributed structure, wherein each structure comprises a PCR chip where PCR is performed;

a rotating means including a shaft that penetrates a center of the PCR module, such that the PCR chip is rotated in accordance with rotation of the shaft; and a temperature zone forming means spaced apart from the PCR chip, capable of applying thermal energy to the PCR chip and allowing the rotating PCR chip to pass through different temperature zones, wherein the shaft of the rotating means is disposed to correspond to a center of the temperature zone forming means, wherein the PCR chip is formed as a single chip that comprises:

a PCR unit where PCR occurs; and a pretreatment unit where a target substance of PCR is separated, and wherein the pretreatment unit comprises:

three chambers, each containing a different one of three aqueous solutions including a sample solution, a washing buffer and an elution buffer, and a capturing means being connected to each of the three chambers, the three chambers including a sample chamber storing the sample solution, a washing buffer chamber storing the washing buffer and an elution buffer chamber storing the elution buffer; and fluid channels, each of which is connected to a corresponding one of the three chambers, wherein:

each fluid channel is hydrophobically treated and has a different cross sectional area, wherein a respective driving force to drive each of the aqueous solutions to flow through a corresponding one of the fluid channels, is determined by a cross sectional area of each fluid channel, such that a hydrophobically-treated fluid channel with a greater cross sectional area requires a smaller driving force;

said respective driving force is generated by a centrifugal force which corresponds to a rotational speed of the PCR chip, such that, when the rotational speed reaches a respective minimum value to generate a corresponding one of said respective driving force for a corresponding one of the fluid channels, a corresponding one of the three aqueous solutions flows to the capturing means via said corresponding one of the fluid channels with a corresponding cross sectional area.

2. The PCR apparatus according to claim 1, wherein the temperature zone forming means is in the form of a disc comprising a plurality of heating blocks.

3. The PCR apparatus according to claim 2, wherein the heating blocks are heated by electric energy and are independently controllable.

4. The PCR apparatus according to claim 2, wherein the heating block comprises a light source generating light energy.

5. The PCR apparatus according to claim 2, wherein the heating block comprises at least one heating block group(s) comprising three unit heating blocks.

6. The PCR apparatus according to claim 2, wherein the heating block comprises two or more heating block groups.

7. The PCR apparatus according to claim 1, wherein the hydrophobically-treated fluid channels include:

a first channel connected to the sample chamber, a second channel connected to the washing buffer chamber, and a third channel connected to the elution buffer chamber, and wherein the PCR unit includes a PCR chamber connected to the capturing means.

8. The PCR apparatus according to claim 1, wherein:

the hydrophobically-treated fluid channels include a first channel connected to the sample chamber, a second channel connected to the washing buffer chamber, and a third channel connected to the elution buffer chamber;

the first channel has a first cross sectional area, the second channel has a second cross sectional area smaller than the first cross section area, and the third channel has a third cross sectional area smaller than the second cross sectional area, such that rotating the chip at or above a first speed; and when the rotational speed reaches a first predetermined value, the sample solution flows from the sample chamber via the first channel to the capturing means;

when the rotational speed reaches a second predetermined value greater than the first predetermined value, the washing buffer flows from the washing buffer chamber via the second channel to the capturing means; and when the rotational speed reaches a third predetermined value greater than the second predetermined value, the elution buffer flows from the elution buffer chamber via the third channel to the capturing means.

* * * * *